(12) United States Patent
Barbera-Guillem et al.

(10) Patent No.: US 6,410,309 B1
(45) Date of Patent: Jun. 25, 2002

(54) CELL CULTURE APPARATUS AND METHODS OF USE

(75) Inventors: Emilio Barbera-Guillem, Powell; M. Bud Nelson, Worthington, both of OH (US)

(73) Assignee: BioCrystal LTD, Westerville, OH (US)

( * ) Notice: Subject to any disclaimer, the term of this patent is extended or adjusted under 35 U.S.C. 154(b) by 2 days.

(21) Appl. No.: 09/724,153

(22) Filed: Nov. 28, 2000

Related U.S. Application Data

(63) Continuation-in-part of application No. 09/526,006, filed on Mar. 15, 2000.
(60) Provisional application No. 60/125,712, filed on Mar. 23, 1999, and provisional application No. 60/133,415, filed on May 11, 1999.

(51) Int. Cl.[7] ................................................ C12M 1/12
(52) U.S. Cl. .................... 435/297.5; 435/394; 435/401; 435/91.4
(58) Field of Search ........................... 435/297.1, 297.2, 435/297.5, 305.1, 305.2, 305.3, 305.4, 383, 394, 401, 91.4

(56) References Cited

U.S. PATENT DOCUMENTS

| 4,435,508 A | * | 3/1984 | Gabridge ..................... 210/445 |
| 4,748,124 A | * | 5/1988 | Vogler ...................... 435/297.1 |
| 5,665,599 A | * | 9/1997 | Minuth ........................ 359/398 |
| 5,817,509 A | * | 10/1998 | Stevens et al. .......... 435/297.5 |
| 5,935,847 A | | 8/1999 | Smith et al. ............. 435/297.5 |

FOREIGN PATENT DOCUMENTS

EP        0 148 161        1/1985

* cited by examiner

Primary Examiner—David A. Redding
(74) Attorney, Agent, or Firm—Benesch, Friedlander, Coplan & Aronoff LLP

(57) ABSTRACT

Provided is a cell culture apparatus for culturing cells, and optionally, for performing magnetic separation of cells desired to be cultured. The cell culture apparatus preferably comprises a frame; at least one gas permeable membrane securely sealed in a leak-proof sealing to a frame and an opposing surface comprising a rigid surface in forming a culture chamber therebetween; and at least one resealable aperture to allow substances to be introduced into, or withdrawn from, the culture chamber.

22 Claims, 4 Drawing Sheets

CELL CULTURE APPARATUS AND METHODS OF USE

This is a continuation-in-part application based on earlier, co-pending application Ser. No. 09/526,006, filed Mar. 15, 2000, which is herein incorporated by reference, which claims benefit of Prov. No. 60/125,712 filed Mar. 23, 1999 and No. 60/133,415 filed May 11, 1999.

FIELD OF THE INVENTION

The present invention generally relates to an apparatus and methods for growing cells or tissue culture in vitro. More particularly, the present invention relates to a cell culture apparatus containing at least one gas permeable membrane which allows rapid and uniform transfer of gases between the environment of cells contained in the cell culture container apparatus and the atmosphere of the incubator in which the cell culture apparatus is incubated.

BACKGROUND OF THE INVENTION

In eukaryotic cell culture systems, the culture of the cells is generally under conditions of controlled pH, temperature, humidity, osmolarity, ion concentrations, and exchange of gases. Regarding the latter, oxygen and carbon dioxide ($CO_2$) are of particular importance to the culturing of cells. In a typical eukaryotic cell culture system, an incubator is provided in which $CO_2$ is infused to maintain an atmosphere of about 5% $CO_2$ within the incubator. The $CO_2$ interacts with the tissue culture medium, particularly its buffering system, in maintaining the pH near physiologic levels. Conventional cell culture containers comprise tissue culture flasks, tissue culture bottles, and tissue culture plates. Entry of $CO_2$ from the incubator atmosphere into a tissue culture plate generally involves a loosely fitting cover which overhangs the plate in excluding particulate contaminants from entering the plate chamber(s), but allows gas exchange between the incubator atmosphere and the atmosphere within the tissue culture plates. Similarly, for a tissue culture flasks or bottle, a loosely fitting cap excludes particulate contaminants from entering the chamber of the flask or bottle, but allows gas exchange between the incubator atmosphere and the atmosphere within the flask or bottle. More recently, a cap is provided with a gas permeable membrane or filter, thereby allowing for gas exchange with a tightly fitting cap.

In addition to $CO_2$, the culturing of cells is dependent upon the ability to supply to the cells a sufficient amount of oxygen necessary for cell respiration and metabolic function. The supply of oxygen for cell respiration in conventional cell culture containers is in the header space of the container, e.g., the void space in the container that is above the surface of the tissue culture medium. Efforts to increase oxygen concentration to the cultured cells includes mechanical stirring, medium perfusion or aeration, increasing the partial pressure of oxygen, and/or increasing the atmospheric pressure. Thus, in conventional cell culture containers the volume or surface provided for gas exchange, as relative to the volume or surfaces of the whole container, is either inefficiently used and/or results in limiting the rate of gas exchange or in the equilibration of gases. This is even more noticeable in small-scale cultures (15 ml or less) in which rate of cell growth, cell densities, and total cell numbers, are frequently low due to space, surface area, and gas exchange limitations.

The rate of gas exchange across gas permeable membranes has been described as "improved". However, gas permeable membranes have been described as undesirable for use in a cell culture system for various reasons. For example, in U.S. Pat. No. 5,523,228, it is taught that a boundary layer of oxygen toxicity forms at the interface between the gas permeable membrane and the tissue culture medium; and further, cells entering into the toxic boundary layer can be irreparably damaged. Further, in U.S. Pat. No. 5,707,869 it is taught that the chemistry of the surface of gas permeable, liquid impermeable materials is incompatible with many cell types; and additionally, due to their propensity to cause non-specific protein binding, such materials can lead to depletion of soluble growth factors.

Thus, there is a need for a cell culture apparatus that can provide an increased surface area for gas exchange as compared to conventional cell culture containers; and which also provides a high rate of cell growth in achieving a high cell density in a relatively short period of time, and with an even distribution of anchorage dependent cells along the attachment surface.

SUMMARY OF THE INVENTION

The present invention provides a cell culture apparatus comprising a frame; at least one membrane which is gas permeable, and wherein the at least one membranes is securely sealed to (in a leak-proof sealing with) the frame, in forming a culture chamber; and at least one resealable aperture through the frame which allows substances to be introduced into, or withdrawn from, the culture chamber.

In one preferred embodiment, the cell culture apparatus comprises a frame over which is extended and securely sealed thereto a gas permeable membrane, and which contains an additional surface comprising a solid plastic in forming a culture chamber therebetween. The frame is sufficiently rigid to provide a housing for assembling the cell culture apparatus of the present invention. The membrane is of suitable thickness to provide sufficient gas permeability to accommodate cell growth in the chamber, and to provide sufficient structural integrity for handling the apparatus. Further, the membrane is of a sufficient optical transparency and clarity so as to observe the cell culture (e.g., the color of the tissue culture medium; and cellular characteristics such as growth and morphology of cells, as observable by microscopy). The frame has at least one resealable aperture, and preferably at least two resealable apertures, which allows substances to be introduced into, or withdrawn from, the culture chamber. Each aperture comprises an opening through the frame which may serve as a passageway into which is guided a portion of an instrument (e.g., needle or pipette or pipette tip) for introducing a substance into or withdrawing a substance from the culture chamber. In a preferred embodiment, the frame is of sufficient thickness and the apertures are of a sufficient limiting diameter to prevent the instrument portion, when inserted through a resealable aperture of the frame, from puncturing either of the walls formed by the membranes of the culture chamber.

The cell culture apparatus provides an unexpected combination of properties including gas exchange and equilibrium, oxygenation of cells cultured in the apparatus, optical transparency and clarity for observing cell culture and cell characteristics during culture, an attachment surface and conditions which promote even distribution of anchorage dependent cells, spatial efficiency, versatility, and conditions which can promote a high rate of cell growth in achieving a high cell density in a relatively short period of time as compared to conventional cell culture devices.

The above and other objects, features, and advantages of the present invention will be apparent in the following Detailed Description of the Invention when read in conjunction with the accompanying drawings in which reference numerals denote the same or similar parts throughout the several illustrated views and embodiments.

DETAILED DESCRIPTION OF THE INVENTION

Definitions

Figure 1:
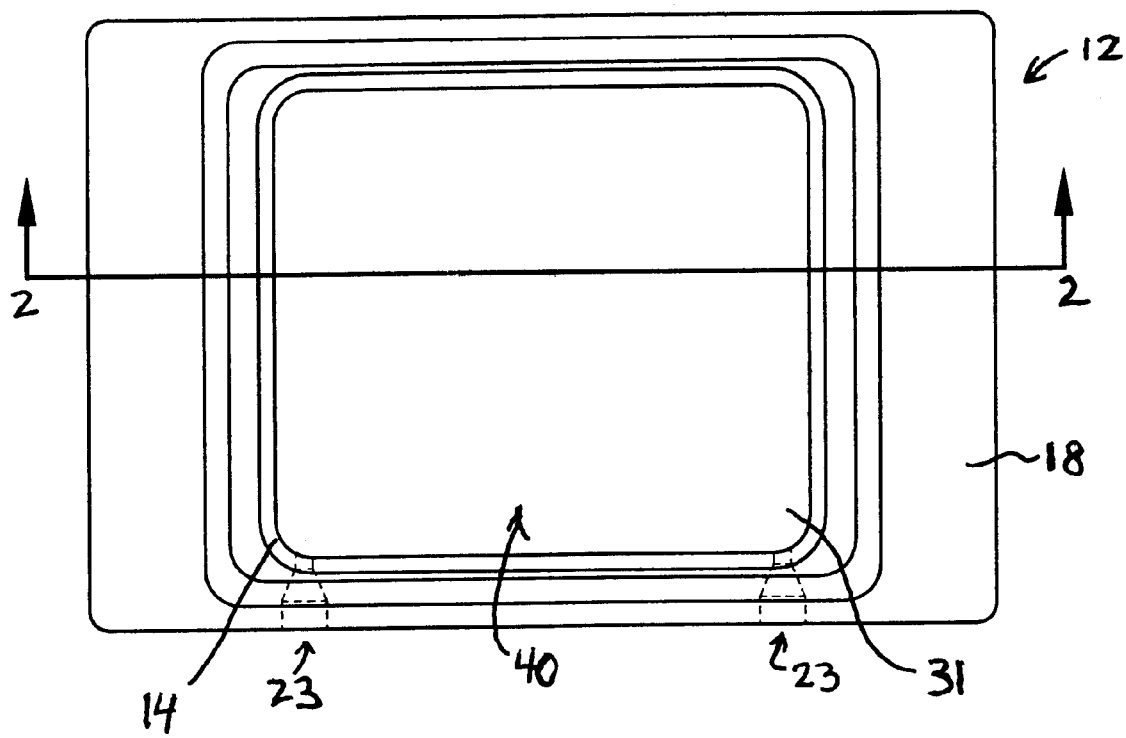
FIG. 1 is a top plan view of an embodiment of a cell culture apparatus according to the present invention.
Figure 2:
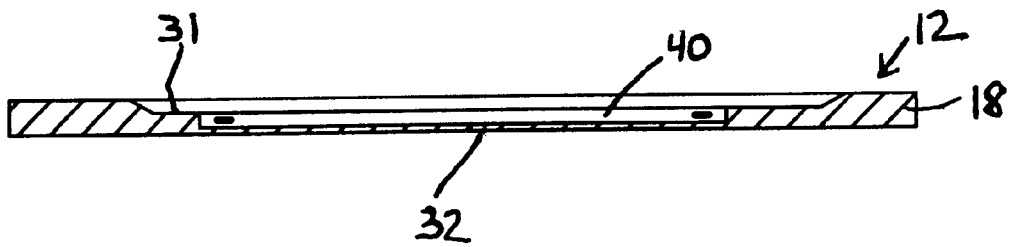
FIG. 2 is a cross-sectional view taken along line 2—2 of the cell culture apparatus illustrated in FIG. 1.
Figure 3:
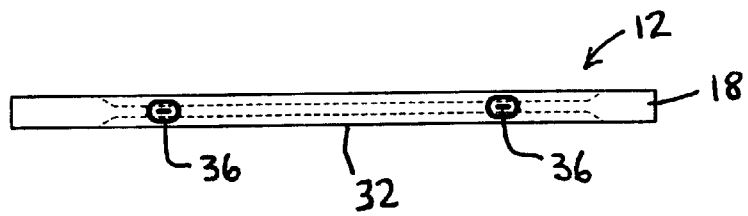
FIG. 3 is a side view of an embodiment of the cell culture apparatus according to the present invention.
Figure 4:
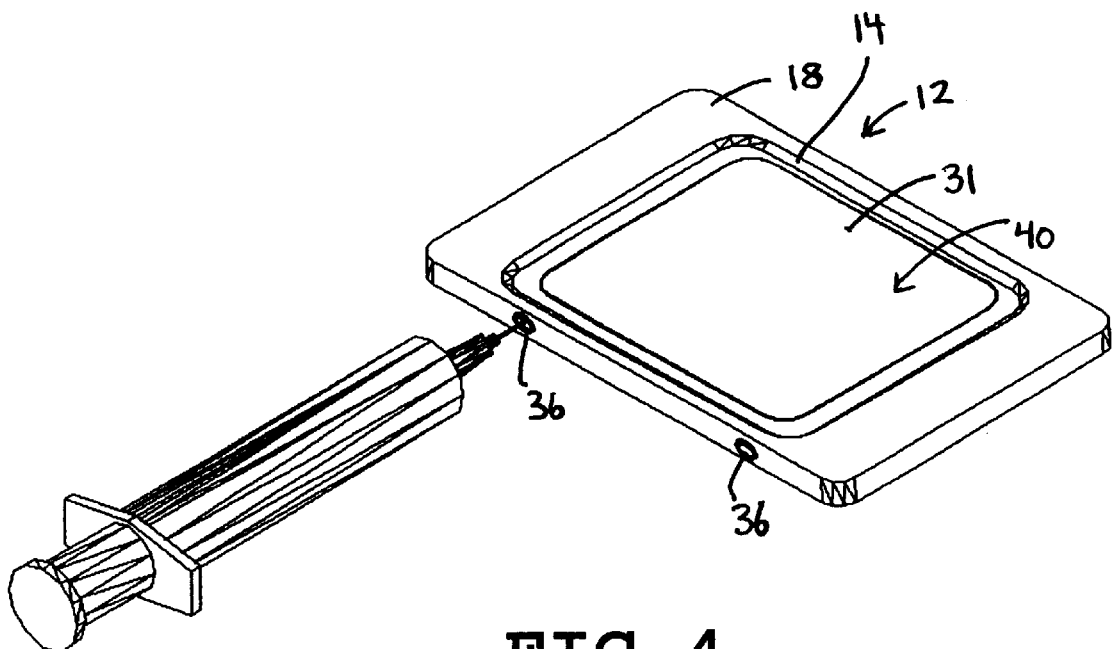
FIG. 4 is a perspective view of a cell culture apparatus showing an embodiment wherein a sample is introduced or withdrawn from the culture chamber.

The term "gas permeable membrane" is used herein, for the purposes of the specification and claims, to mean a biocompatible material which is liquid impermeable, which is capable of allowing transfer of gases into and out of the cell culture chamber, and which is capable of excluding microbial contamination (e.g., pore size is sufficiently small enough to exclude passage of microbes commonly encountered in contamination of cell cultures), and which is optically transparent and clear for permitting observation of the cell culture (e.g., of the color of the tissue culture medium which contains a pH indicator; and of cultured cell characteristics such as growth and morphology of the cells as detectable by light microscopy), as will be described in more detail herein. Thickness of the gas permeable membrane will depend on the desired resultant characteristics which may include, but are not limited to, structural integrity, degree of gas permeability, and rate of transfer of gases. In general, the thickness of a gas permeable membrane can range from less than about 0.00125 inches to about 0.005 inches. In a preferred embodiment, the thickness of the membrane is in the range of about 0.002 inches to about 0.004 inches, and in a more preferred embodiment, 0.004 inches. The gas permeable membrane may be comprised of one or more membranes known in the art. Membranes typically comprise suitable polymers that may include polystyrene, polyethylene, polycarbonate, polyolefin, ethylene vinyl acetate, polypropylene, polysulfone, polytetrafluoroethylene, or a silicone copolymer. The choice of the composition of the gas permeable membrane will depend on the type of cell to be cultured (e.g., cells which grow attached (anchorage-dependent), cells which grow in suspension (anchorage-independent), cells that may grow as attached or in suspension), degree of gas permeability, rate of transfer of gases, and optical transparency and clarity. In a more preferred embodiment, the gas permeable membrane has been treated, on a side of the membrane which may serve as a surface for attachment of anchorage-dependent cells in culture, by ionization to improve adhesion of the treated membrane surface to anchorage-dependent cells. Ionization of the membrane may render the treated membrane surface more hydrophilic, and can be performed using methods known in the art which include plasma discharge, corona discharge, gas plasma discharge, ion bombardment, ionizing radiation, and high intensity UV light. In a preferred embodiment for promoting growth of anchorage-independent cells, the gas permeable membrane is not treated by ionization. In a preferred embodiment, the gas permeable membrane is a single membrane comprised of polystyrene or polypropylene, is treated on at least one side by corona treatment, and is about 0.004 inches thick. In a preferred embodiment, the at least one gas permeable membrane of the cell culture apparatus according to the present invention has the following gas permeability characteristics with respect to oxygen and carbon dioxide gases: permeability performance at 1 atmosphere and at 37° C. for $O_2$ is in the range of from about 15 to about 40 Barrers, and more preferably about 23 Barrers; and permeability performance at 1 atmosphere and at 37° C. for $CO_2$ is in the range of from about 80 to about 95 Barrers, and more preferably about 88 Barrers.

The terms "optically transparent and clear" is used herein, and in relation to characteristics of a gas permeable membrane and for observation of cells cultured in the cell culture apparatus according to the present invention, for the purposes of the specification and claims, to mean that a gas permeable membrane is clear and transparent, and more preferably: is transparent in the spectrum range of from about 250 nm to about 900 nm; lacks fluorescence under excitation light when the excitation light has a spectrum in the range of from about 260 nm to about 700 nm; and has a sharper diffraction image as compared to the diffraction image of a conventional, plastic tissue culture flask or tissue culture plate. Regarding the latter, an indelible black ink marker was used to draw a line of about 1 mm in width on both the gas permeable membrane of a cell culture apparatus according to the present invention, and the hard plastic surface of a tissue culture flask. Using a 20× objective and a standard light microscope, the line observed on the gas permeable membrane remained a well-defined line of about 1 mm. In contrast, a diffused image of the line was observed on the tissue culture flask surface; i.e., the width of the line observed was approximately 3 mm, with the main line being surrounded by dark shadows in which contrast was lost. Thus, the tissue culture flask surface demonstrated a diffraction image that is at least 100% greater than that observed for the membrane surface of the cell culture apparatus according to the present invention.

The term "magnetic sheet assembly" is used herein, for purposes of the specification and claims, to mean an assembled combination comprising, in structural order, a magnetic sheet, a permanent adhesive, a carrier sheet, and a non-permanent adhesive which together is particularly adapted to permit ready adhesion to and removal from a surface of the cell culture apparatus according to the present invention in an application for magnetic separation. The magnetic sheet assembly may further comprise a layer in contact with the magnetic sheet on a side opposite to the permanent adhesive, wherein the layer may be a material selected from the group consisting of a protective coating, a label, and a combination thereof. Various protective coatings for magnets are known in the art to include, but are not limited to, polyurethane, a polyurethane rubber compound, polyester, polyester-imide, polyamide, and the like; and may further comprise a colorant. A preferred magnetic sheet assembly is described in more detail in copending application Ser. No. 09/526,006 (the disclosure of which is herein incorporated by reference). Briefly, a magnetic sheet comprises at least one substantially flat magnetic sheet having the following characteristics: (a) a surface magnetic field having a field strength, as measured by a gaussmeter, in a range of from about 250 to about 1500 gauss, and more preferably in a range of from about 450 to about 1200 gauss; (b) sufficient flexibility to permit the magnetic sheet, as part of an assembly, to be separated from the cell culture apparatus to which it is removably adhered by pulling the magnetic sheet apart from the apparatus; (c) is magnetized with magnetic poles of alternating polarities, which poles being generally arranged as a plurality of parallel, spaced apart lines that are spaced to maximize efficiency of magnetic separation (in a preferred embodiment, 7 to 9 poles per inch), and may further comprise magnetic poles which are positioned to form a combination of a plurality of parallel spaced apart lines and a plurality of perpendicular spaced apart lines in forming a grid pattern for maximizing efficiency of magnetic separation (in a preferred embodiment, 14 to 18 poles per inch); and (d) is generally dimensionally coextensive with the surface to which the magnetic sheet assembly is to be removably adhered. A magnetic sheet may include, but is not limited to, a sheet consisting of a fine magnetic powder such as barium ferrite loaded into a thermoplastic binder; a sheet of plastics or vinyl material impregnated with a ferromagnetic material; a sheet of synthetic resin material having mixed therein a magnetic powder; magnetic particles embedded in a polymer sheet of typically 0.7 mm or 0.030 inches thickness; a vinyl material including magnetic materials dispersed therethrough; or other suitable material having properties compatible with its intended purpose. In a preferred embodiment, the magnetic sheet is comprised of a flexible barium ferrite magnet material, or a flexible strontium ferrite magnet material, or a neodymium iron boron bonded magnetic material, or a combination thereof. As apparent to those skilled in the art, the thickness of the magnetic sheet will vary depending on factors which include, but are not limited to, the composition of the magnetic sheet material, whether the magnetic sheet comprises one or more sheets, the desired field strength, and the spacing of the magnetic poles. In that regard, and for purposes of illustration but not limitation, the thickness of the magnetic sheet may range from about 0.2 mm to about 5 mm. A preferred thickness of a suitable commercially available, flexible strontium ferrite-based material of from about 450 Gauss to about 1000 Gauss is in a range of from about 0.03 to about 0.06 inches. A pressure sensitive permanent adhesive is provided to fixedly bond the magnetic sheet to the pressure sensitive adhesive laminate comprising the pressure sensitive permanent adhesive, the carrier sheet, and the pressure sensitive non-permanent adhesive. Conventional pressure sensitive permanent adhesives are well known in the art, are commercially available from adhesive manufacturers, and include, but are not limited to, acrylic base adhesives, rubber based adhesives, and the like. A typical thickness of the pressure sensitive permanent adhesive or the pressure sensitive non-permanent adhesive may be in a range of from about 0.0003 to about 0.003 inches; and more preferably, is about 0.0005 inches. The pressure sensitive permanent adhesive and pressure sensitive non-permanent adhesive may be applied to a respective separate side of the carrier sheet, in fabricating the double-sided pressure sensitive adhesive laminate, by any conventional method known in the art such as by coating (e.g., brush coating, knife coating, transfer coating, roll coating, and the like), dispersion, spraying, calendaring, and the like. The pressure sensitive non-permanent adhesive is: (a) of sufficient cohesion to keep the magnetic sheet assembly in adhesive contact with the surface of the cell culture apparatus for a prescribed period of time necessary for a magnetic separation process to be initiated and completed (typically a time in a range of from about 10 minutes to about 4 hours); and (b) is of a light to moderate tack to permit the magnetic sheet assembly to be lifted (e.g., peeled) from the cell culture apparatus to which it was in close adhesive contact, wherein the non-permanent adhesive releases clearly (0% to less than 5% of the surface covered by the adhesive retains any visible adhesive residue upon removal) from the surface of the cell culture apparatus as the magnetic sheet assembly is removed. Conventional pressure sensitive non-permanent adhesives, particularly suited for the intended purpose as outlined above, are well known in the art, are commercially available from adhesive manufacturers, and may include, but are not limited to, synthetic or natural rubber based adhesive compositions, acrylic based adhesive composition, and the like. The carrier sheet may be selected from a variety of carrier sheet materials suitable for use with pressure-sensitive adhesive products. The carrier sheet is generally thin and flexible, and preferably the carrier sheet has a thickness in the range of from about 0.03 mm to about 0.25 mm; and more preferably, the carrier sheet has a thickness of about 0.002 inches. The carrier sheet material may be fibrous, non-fibrous, or a combination thereof. The carrier sheet may be a suitable polymeric film, fabric (e.g., nylon), paper, cellulose, and the like; and may preferably include, but is not limited to, a polystyrene, an acrylic polymer (e.g., polymethylmethacrylate), a vinyl polymer (e.g., vinyl chloride or ester, plasticized vinyl polymer, and the like), a polycarbonate, a polyolefin, a polyester, a cellulose acetate.

The term "septum" is used herein, for the purposes of the specification and claims, to mean a pre-slit septum comprised of an elastomeric material dimensioned to cause centrally directed compression, when inserted in an access port configured to accommodate the septum, such that: when a tip is inserted into and accesses the slit of the septum access port assembly, the slit closes around and sealingly engages the outer surface of a tip accessing the septum to prevent leakage between the tip and slit so as to maintain a leak-proof seal; and enhances the ability of the septum to reseal itself ("resealability") after withdrawal of the tip from the slit, even after the septum has been repeatedly accessed by tips. Preferred septums are described in more detail in co-pending application Ser. No. 09/724,251 (the disclosure of which is herein incorporated by reference). The septum may further comprise one or more additives such as a colorant, filler, and the like. The elastomeric material may be natural or synthetic and may be a material including, but not limited to, silicone rubber, fluorocarbon rubber, butyl rubber, polychloroprene rubber, a silicone elastomer composite material, thermoplastic elastomer, medical grades of silicone rubber, polyisoprene, a synthetic isoprene, and a combination thereof. The elastomeric material may be selected to have a Shore A durometer within the range of from about 30 to about 80. In a preferred embodiment, the septum comprises an elastomeric material and an antimicrobial agent mixed and formed into the elastomeric septum, wherein the antimicrobial agent becomes incorporated into the elastomeric septum and forms a surface coating on the elastomeric septum, and wherein the antimicrobial agent exhibits migration through the elastomeric septum as the surface coating of antimicrobial agent is depleted. Suitable and exemplary broad spectrum antimicrobial agents may include, but are not limited to, triclosan (2,4,4'-trichloro-2'hydroxydiphenyl ether), 5-chloro-2-(2,4-dichlorophenoxy)phenol, and 2-2'-methylene-bis-4-chlorophenol, 3-(trifluomethyl)-4,4'-dichlorocarbanilide, or polyhexamethylene biguanide hydrochloride.

The term "tissue culture medium" is used herein, for the purposes of the specification and claims, to mean a liquid solution which is used to provide sufficient nutrients (e.g., vitamins, amino acids, essential nutrients, salts, and the like) and properties (e.g., osmolarity, buffering) to maintain living cells (or living cells in a tissue) and support their growth. Commercially available tissue culture medium is known to those skilled in the art.

EXAMPLE 1

In this example, illustrated are various embodiments of the cell culture apparatus according to the present invention. However, in all embodiments of the cell culture apparatus according to the present invention described herein in this Example and the following Examples, an essential feature is that the culture chamber formed therein comprises at least one gas permeable membrane. Referring now to FIGS. 1–7, the cell culture apparatus 12 comprises frame 18. Frame 18 may be of a basic biocompatible composition that may comprise suitable plastic, thermoplastic, synthetic, or natural materials which can be fabricated into a framework structure, thereby achieving the required structural integrity for its intended purpose. It should be apparent to those skilled in the art that a wide latitude of choice can be exercised in selecting a material suitable for formation and/or fabrication of frame 18. The dimensions of cell culture apparatus 12, and frame 18, may depend on one or more factors including, but not limited to, the desired fluid capacity of the culture chamber formed therewith, and the dimensions of the culture chamber. In a preferred embodiment, cell culture apparatus 12 is of a general shape and size to be able to be accommodated, and be substantially held in position, by a standard mechanical stage specimen holder for a microscope. In a more preferred embodiment, cell culture apparatus 12 (and frame 18) has a length in a range of from about 10 cm to about 13.5 cm, a width in a range of from about 7 cm to about 9 cm, and a ing, sonic welding, pressure fit sealing in forming a leak-proof seal, and a molding process in which the membranes become an integral part of the frame (e.g., by extrusion). In a preferred embodiment, the membrane is secured to the frame by a sonic welding process which comprises cutting the frame and bonding (melting) the membrane to substantially the cut portion of the frame in a manner which results in a leak-proof sealing between the membrane secured to the frame in the formation of a culture chamber, in a process of assembling the cell culture apparatus according to the present invention.

As will become apparent to one skilled in the art from the description herein, membrane 31 (or a portion thereof) may be removed from frame 18 so as to facilitate further manipulations of cells cultured in the culture chamber of the cell culture apparatus according to the present invention. In one embodiment where anchorage-dependent cells are cultured, membrane 31, to which is attached the anchorage-dependent cells, is removed from the frame by cutting it or peeling it away from the frame. Alternatively, the membrane does not serve as the attachment surface for anchorage-dependent cells (e.g., surface 32 serves as the attachment surface) but is cut or peeled from the frame so as to access the culture chamber 40 and the cells contained therein. In the case where anchorage-dependent cells are attached to the membrane, the membrane may then be directly stained using standard dyes or stains, and methods for staining known to those skilled in the art. For example, the attached cells may be stained for analysis by fluorescence microscopy, phase contrast microscopy, Nomarsky contrast microscopy, scanning electron microscopy, and imaging (e.g., photography or digital imaging) height in a range of from about 0.2 cm to about 2.0 cm; and more preferably is about 12.6 cm in length by about 8.4 cm in width by about 0.5 cm in height; providing a cell culture apparatus which permits culturing of cells in less incubator space than would be required for culturing cells at a comparable growth rate or to a comparable cell density using a conventional cell culture device. In a preferred embodiment, and in referring to FIGS. 1 & 4–7, a beveled portion 14 of frame 18 slopes at an angle (e.g., at a degree in a range of from about 25° to about 40°), in relation to the plane of the at least one gas permeable membrane.

Referring now to FIGS. 1–6, frame 18 is a housing shaped to accommodate the aligning, contacting and securing thereto (in a leak-proof sealing) gas permeable membrane 31 in assembling cell culture apparatus 12 of the present invention. Frame 18 may further comprise a box-like housing. Also provided is another surface 32 which forms a wall of cell culture chamber 40. Surface 32 is a rigid surface preferably formed as part of frame 18 by a single molding operation, and preferably comprises a high-density resinous material which may include, but is not limited to, polyethylene, polypropylene, polyvinylchloride, or other plastic suitable for cell culture applications. Surface 32 is liquid impermeable and gas impermeable. Membrane 31 may be secured to frame 18 in a leak-proof sealing using means that may include mechanical means, chemical means (an adhesive agent which may include, but is not limited to, a pressure-sensitive acrylic adhesive, hot-melt adhesive, rubber cement, or any other form of adhesive or bonding agent useful for the purposes attendant to the present invention), or other suitable means. Regarding the latter, other suitable means may include one or more of heat bond-associated therewith. Alternately, the attached cells may be gently scraped off membrane 31 or surface 32 (depending which serves as the attachment surface) in circumstances where it is desirable to harvest the cells off of the membrane without enzyme treatment (e.g. trypsinization). Such circumstances may include further use or analysis of the harvested cells where a trypsin-sensitive cell surface molecule is needed to be intact; e.g., for immediate, further analysis such as in flow cytometric analysis, or in a functional bioassay (e.g., cell cytotoxicity assay).

As shown in FIGS. 1–7, frame 18 has at least one aperture 23, and preferably at least two apertures. As previously described herein, aperture 23 of frame 18 may serve as a passageway into which is guided an instrument for introducing a substance into, or withdrawing a substance from, or venting from, the culture chamber. Thus, the diameter of each aperture 23 is sufficient to allow for entry of that portion of the instrument (for reference purposes only, referred to hereinafter as "tip" of the instrument) which is necessary for its intended purpose of introducing a substance into, or withdrawing a substance from, or venting from, the culture chamber. As will be apparent to one skilled in the art, the diameter of each aperture 23 will depend on the type of instrument being used for the intended purpose, and the size of the tip of the instrument. For example, where the instrument is a syringe and blunt tip, the diameter of each aperture 23 is sufficient to allow the tip to pass therethrough (e.g., about 1 mm to about 2 mm in diameter). The tip of the instrument is guided through aperture 23 of frame 18, and introduced into culture chamber 40. In a preferred embodiment, the frame is of sufficient thickness and one or more of apertures 23 are of a sufficient limiting diameter to prevent the tip of the instrument, when inserted through aperture 23, from contacting and puncturing either of the walls of the culture chamber 40 formed by membranes 31 and 32. The at least one aperture 23 is resealable by a suitable means known in the art; e.g., a cap, a plug, a septum, or other suitable means. With reference to FIGS. 3–6 & 8, and in one preferred embodiment, aperture 23 is substantially (partially or completely) filled and sealed with a septum 36, and more preferably with a septum comprising an elastomeric material and an antimicrobial agent as previously described herein in more detail.

Figure 5:
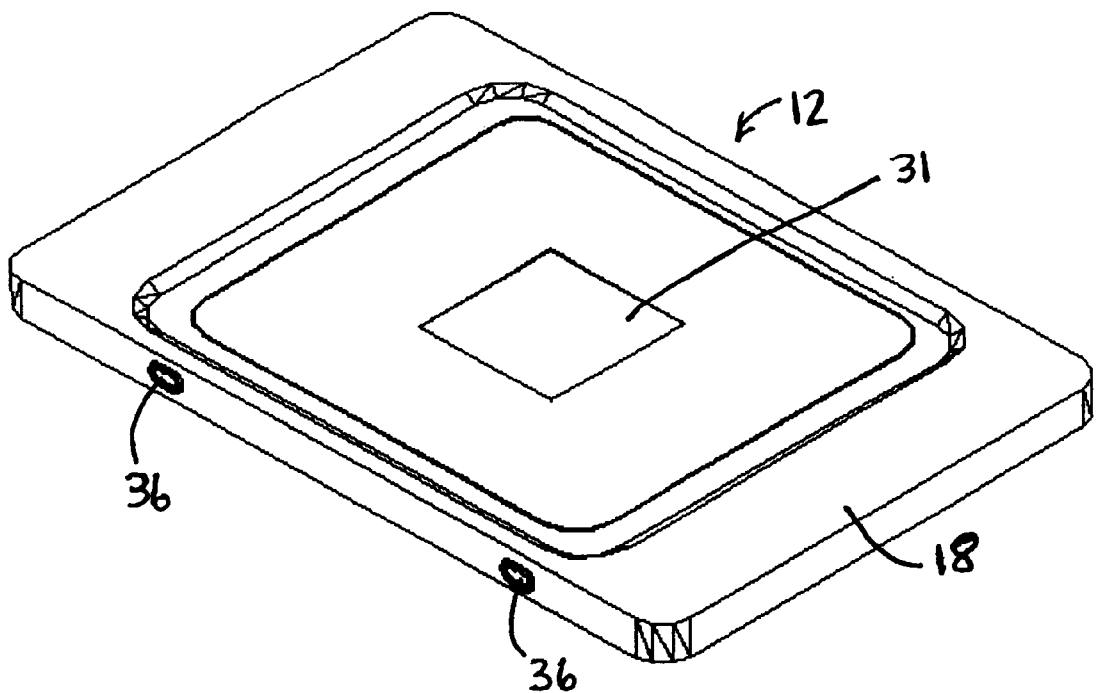
FIG. 5 is a perspective view of another embodiment of the cell culture apparatus according to the present invention.
Figure 6:
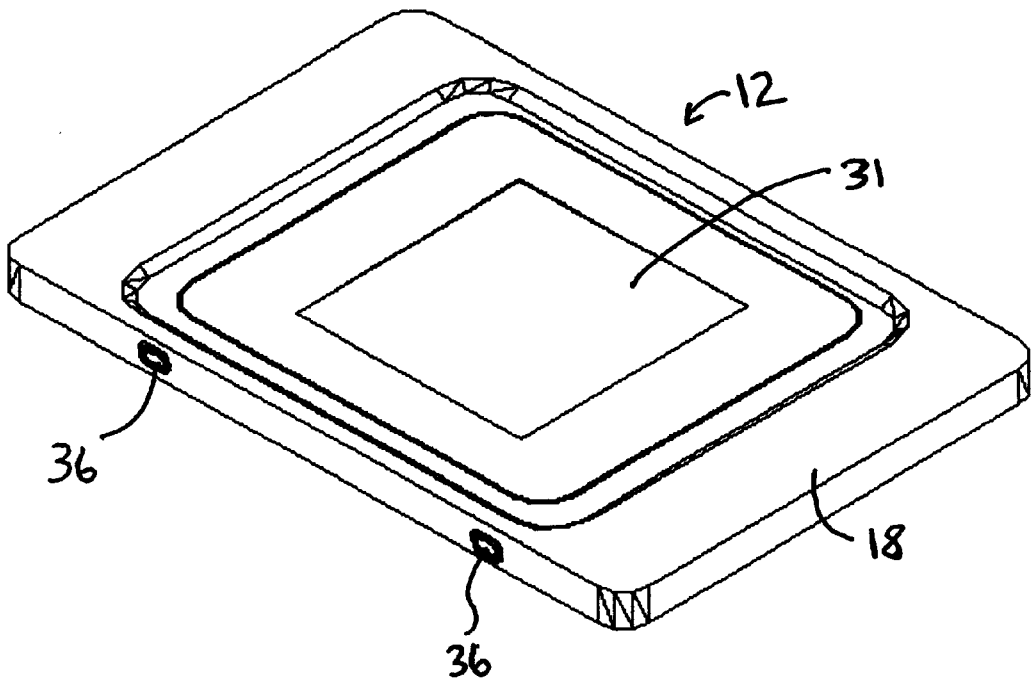
FIG. 6 is a top view of another embodiment of the cell culture apparatus according to the present invention.
Figure 7:
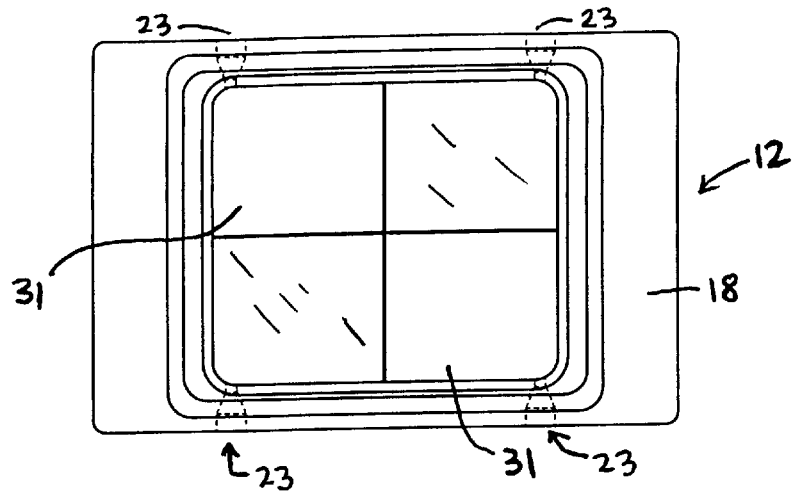
FIG. 7 is a top view of another embodiment of the cell culture apparatus according to the present invention.
Figure 8:
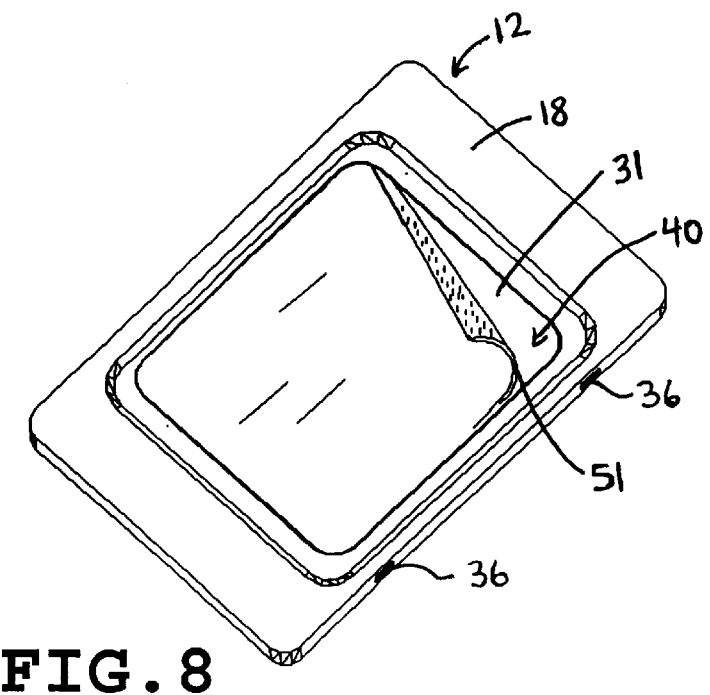
FIG. 8 is a perspective view of a cell culture apparatus showing removal of a magnetic sheet assembly which is detachably secured in adhesive contact to the cell culture apparatus.

Turning now to the gas permeable membrane, the gas permeable membrane forms a portion in the range of from about 10% to about 100% of a surface forming the wall of the culture chamber in the cell culture apparatus according to the present invention. In that regard, FIGS. 1, & 8 show a gas permeable membrane comprising the entire surface of a wall forming culture chamber 40. FIGS. 5 & 6 show a single gas permeable membrane forming about 10% and about 60%, respectively, of the surface of a wall forming culture chamber 40. FIG. 7 illustrates a plurality of gas permeable membranes which together form about 50% of the surface of a wall forming culture chamber 40. In using a gas permeable membrane as substantially all of an attachment surface in the culture chamber of the cell culture apparatus according to the present invention, it has been observed that anchorage-dependent cells tend to grow relatively uniformly over the entire attachment surface (including the edges of the chamber) during culture. It is believed that this absence of significant variability in cell attachment and growth over the entire attachment surface is due to the relative absence of variability in gas (e.g., oxygen and ty, and conditions which can promote a high rate of cell growth in achieving a high cell density in a relatively short period of time. For example, anchorage-dependent cells may be introduced into the cell culture apparatus, and the cells introduced are incubated a sufficient time (depending on the cell type) to allow settling by gravity, and attachment of the cells to gas permeable membrane 31. The cell culture apparatus may then be rotated 180° so that the inverted cells are grown in a culture as suspended from membrane 31. Additional cells may then be seeded on surface 32. Preferably, membrane 31 is optically transparent and clear; e.g., in facilitating observations of changes in the color of the medium's pH indicator typically observed during cell culture, and of cellular characteristics (e.g., growth and morphology of cells such as by microscopy).

In an additional embodiment, a bioreactor comprises a plurality of the cell culture apparatuses according to the present invention which are operatively linked by providing a fluid passageway connecting the culture chambers of the plurality of cell culture apparatuses. To facilitate culturing of cells in such a bioreactor environment, each of the plurality of the cell culture apparatuses may be interconnected with another cell culture apparatus by a connecting passageway that allows for the flow of tissue culture medium through the passageway and between the culture chambers of the interconnected cell culture apparatuses. One example of interconnecting a first cell culture apparatus to a second cell culture apparatus in forming a bioreactor is by the use of a piece of sterile tubing interposed between two syringe needles. One needle would be inserted into a resealable aperture 23, through the frame, and into a culture chamber of the first cell culture apparatus; and the carbon dioxide) exchange across the length and width of the gas permeable membrane in the culture chamber as provided by the cell culture apparatus according to one embodiment of the present invention. Thus, in the cell culture apparatus according to the present invention, the gas permeable membrane provides an attachment surface which provides for a higher density of, and spatial efficiency for, anchorage-dependent cell growth. This is an advantage over conventional cell culture containers which have been reported to exhibit non-uniform gas exchange over the respective attachment surface; and hence, a variability in the ability of cells to grow depending on their spatial relation to the gradient of gas exchange.

As will be apparent to one skilled in the art from the description contained herein, the distance between membrane 31 and surface 32 depends on the size (e.g., the height) of frame 18. Although there is no general relative restriction on either the shape or size of culture chamber 40, in a preferred embodiment for culturing to achieve a high density of cells, the average distance between membrane 31 and surface 32 is in a range of from about 0.05 to about 0.5 inches. In a more preferred embodiment, the average distance between membrane 31 and surface 32 is a distance in the range of from about 0.07 to about 0.08 inches. In a preferred embodiment, anchorage-dependent cells are cultured in the cell culture apparatus with membrane 31 as the surface to which the anchorage-dependent cells may attach, and is a surface which provides uniform gas exchange. By rotating the cell culture apparatus according to the present invention to allow both membrane 31 and surface 32 to simultaneously serve as surfaces for attachment of anchorage-dependent cells, provided are spatial efficiency, versatili-second needle would be inserted into a resealable aperture 23, through the frame, and into a culture chamber of a second cell culture apparatus. A piece of tubing may then have one open end operatively connected to the first needle, and the opposite open end of the tubing operatively connected to the second needle. The tubing, located between and operatively connected to the two needles, provides fluid flow communication between the culture chamber of the first cell culture apparatus and the culture chamber of the second cell culture apparatus. Using similar methodology and a plurality of tubing, a plurality of the cell culture apparatuses may be operatively connected in forming a bioreactor.

EXAMPLE 2

In this example, illustrated are various embodiments of using the cell culture apparatus according to the present invention to culture cells, whether the cells are individual cells (cells which are grown independent of forming a structure such as a tissue; an illustrative example being a cell line), or cells forming a tissue (typically, a mesh or network of cells, with their intercellular substance in forming a structured or organized tissue), or a combination thereof. It will be apparent to one skilled in the art that individual cells which can be cultured in the cell culture apparatus comprise one or more cell types including, but not limited to, animal cells, insect cells, mammalian cells, human cells, transgenic cells, genetically engineered cells, transformed cells, cell lines, anchorage-dependent cells, and anchorage-independent cells. It will be also apparent to one skilled in the art, that tissue formed by cells in culture can also be cultured in the cell culture apparatus according to the present invention. It will further be apparent to one skilled in the art that the cell culture apparatus of the present invention is generally not limited to a specific type of cell to be cultured, nor the tissue culture medium capable of sustaining cell growth as long as the medium provides sufficient nutrients and properties (e.g., osmotic pressure) to maintain and support cell growth. Further, it will be apparent to one skilled in the art that prior to use for culturing cells, the cell culture apparatus in sterilized using a method conventional in the art. In a preferred embodiment, the cell culture apparatus in sterilized by exposure to gamma radiation.

In one embodiment, anchorage-dependent cells are cultured in the cell culture apparatus according to the present invention. For growing anchorage-dependent cells, either membrane 31, or surface 32, or both, has an inner face (forming an inside surface of the culture chamber) which is of sufficient hydrophilicity for promoting adhesion of cells desire to be cultured; and therefore, can act as a surface to which the cells can attach and grow. For example, the at least one membrane 31 may have inherent chemical properties which promote such adhesion, or the inner face may be treated (e.g., electrically, ionically, or chemically) to promote such adhesion. It will be apparent to one skilled in the art that such treatment may include one or more of chemically etching of the inner surface, ionization of the inner surface, or coating the inner surface with a suitable coating reagent. Suitable coating reagents are known to those skilled in the art to include gelatin, collagen, fibronectin, an adhesion protein, an adhesion peptide (see, e.g., PCT/US95/00817).

A method of culturing cells using the cell culture apparatus according to the present invention comprises suspending the cells to be cultured (e.g., anchorage-dependent cells or anchorage-independent cells) in an appropriate amount of tissue culture medium to support cell growth, in forming a suspension; introducing the suspension into a suitable instrument (e.g., a syringe and blunt tip combination) for injecting the suspension into the cell culture apparatus; using sterile (aseptic) technique, and inserting a portion (e.g., the tip of a needle) of the instrument through a resealable aperture (septum an aperture combination) and into the cell culture chamber of the cell culture apparatus; expelling the suspension from the instrument (e.g., from the chamber of a syringe and through the tip) and into the cell culture chamber; withdrawing the tip from the cell culture apparatus; and incubating the cell culture apparatus, containing the suspension of medium and cells (e.g., in a cell culture incubator or in conditions sufficient for cell growth as known in the art including suitable temperature, $CO_2$ and $O_2$ concentrations). It will be apparent to those skilled in the art that a substance that may be introduced into the culture chamber of the cell culture apparatus may include one or more of tissue culture medium alone, tissue culture medium with cells, cells suspended in a physiological buffer, and a drug or cytokine or growth factor or enzyme (e.g., solution of trypsin) or other biological agent to treat cells cultured therein.

In a preferred embodiment, and for applications in which a high growth rate of cells is desired, in a method of culturing cells in the cell culture apparatus according to the present invention, the cell culture chamber may be filled completely with tissue culture medium or other suitable growth medium for culturing cells or tissue desire to be grown. It will be apparent to one skilled in the art that completely filling the culture chamber means that there is substantially no head space (e.g., air bubbles) remaining in the culture chamber. It is noted that there can be an abrupt, initial rise in the pH of tissue culture medium within the first hour or two in conventional cell culture containers due mainly to the distribution of dissolved $CO_2$ between the medium and the gas phase. This pH change has mostly occurred within the first hour of incubation, well before cells are capable of producing significant amounts of $CO_2$. The resultant pH change negatively affects the rate of cell growth until the cells are in sufficient number to restore the optimal $CO_2$ level by providing $CO_2$ through cell respiration. However, unlike the conventional cell culture containers, in a preferred embodiment, the cell culture apparatus according to the present invention can be filled in a manner wherein a substantial head space is lacking. Further, the cell culture apparatus of the present invention provides an unexpected capacity for gas equilibrium believed to be due to the enhanced gas exchange exhibited by the use and arrangement of one or more gas permeable membranes. Together, these features of the cell culture apparatus according to the present invention prevent the abrupt change in initial pH as observed in conventional cell culture containers. By preventing such an abrupt change in pH of the medium, the initial culture conditions attain a pH equilibrium more conducive to optimal cell growth. Thus, a disadvantage of conventional cell culture containers, as opposed to the cell culture apparatus according to the present invention, is that conventional cell culture containers require a head space between the top of the container and the surface of the tissue culture medium. Additionally, in a method of culturing cells in the cell culture apparatus according to the present invention, wherein the culture chamber is filled in a manner wherein a substantial head space is lacking, the cell culture apparatus may be tilted or gently shaken to mix the medium and cells contained therein, without causing detectable foam formation or cell trauma. In particular, the at least one gas permeable membrane may be secured taut to the frame so that the membrane is tympanic and thereby facilitates mixing in the filled culture chamber.

In an additional embodiment of a method of culturing cells using the cell culture apparatus according to the present invention, the method comprises suspending anchorage-dependent cells to be cultured in an appropriate amount of tissue culture medium to support cell growth, in forming a suspension; introducing the suspension into a suitable instrument for injecting the suspension into the cell culture apparatus via one or more resealable apertures; using sterile (aseptic) technique, and inserting a tip of the instrument through one or more resealable apertures and into the cell culture chamber of the cell culture apparatus; expelling the suspension through the tip of the instrument and into the cell culture chamber; withdrawing the tip of instrument from the cell culture apparatus; and incubating the cell culture apparatus, containing the suspension of medium and cells, for a sufficient time (e.g., 30 minutes to 3 hours, depending on the cell type) to allow the cells to settle by gravity, and contact and attach to the membrane serving as the attachment surface. The method may further comprise subsequently rotating the cell culture apparatus 180°, and placing the cell culture apparatus in the incubator in a position so that the cells are incubated in an inverted manner in the culture chamber; i.e., the cells are attached to the membrane serving as the upper wall of the culture chamber with respect to the incubator shelf on which the cell culture apparatus rests. Hence, in this embodiment, the cells hang down into the culture chamber, and grow suspended along the surface of the upper membrane. This allows cell debris to fall by gravity, from the suspended culture, to the lower surface where such separated cell debris may be easily removed from the culture chamber by aspiration and or a washing step.

EXAMPLE 3

The cell culture apparatus may also be used for magnetic separation applications. In this example, illustrated are various embodiments wherein the cell culture apparatus further comprises a magnetic sheet detachably secured thereto. In one embodiment, and in referring now to FIG. 8, a magnetic sheet assembly 51 is extended over and detachably secured to cell culture apparatus 12 in a face to face manner such that the magnetic sheet is placed in a position so as to be in adhesive contact with substantially all (all or that portion of the membrane which forms a wall of culture chamber 40) of the surface of the at least one gas permeable membrane of the cell culture apparatus. The magnetic sheet assembly may be detachably secured to the cell culture apparatus in a manner for magnetic particles placed within the culture chamber 40 to be attracted to, and held into position (along the inside wall of culture chamber 40 comprising the inner surface of the membrane 31) by, the magnetic field strength of the detachably secured magnetic sheet assembly. In a preferred embodiment, magnetic sheet assembly 51 has a form generally co-dimensional with the membrane to which it is placed in adhesive contact. In a method of magnetic separation using the cell culture apparatus having detachably secured thereto a magnetic sheet assembly, and using methods described in the previous Examples herein, introduced into the culture chamber are: (a) a fluid containing a mixed population of cells in which there is a population of target cells (e.g., the cell type desired to be isolated from the fluid containing the mixed population of cells types); and (b) a magnetic separation reagent comprising magnetic particles coated with a ligand, wherein the ligand has sufficient binding specificity and affinity for the cells desired to be separated and for achieving magnetic separation. After mixing the contents together for a sufficient time for contact and binding interactions between the magnetic separation reagent and the target cells to occur, the magnetic separation reagent contacts and binds, via the ligand coating, with target cells present in the fluid in forming complexes. It will be apparent to one skilled in the art that the fluid containing the mixed population of cells, and the magnetic separation reagent may be mixed first, and then the mixture is introduced in the cell culture apparatus for performing the magnetic separation. In either embodiment, complexes formed are drawn to (by magnetic attraction), and contact the wall of culture chamber 40 comprising the inner face of the membrane, along the plane of cell culture apparatus to which is detachably secured the magnetic sheet. After allowing for a sufficient time for complexes to be held into position along the membrane, the fluid is removed from the cell culture apparatus. In a method of negative selection, the removed fluid is utilized because it has been depleted of a specific cell population. In a process of positive selection, because the cell type desired to be separated is held in position by magnetic attraction and as complexes in the culture chamber, the removed fluid contains substantially all of the (unwanted) remainder of the mixed cell populations. In this positive selection process, culture chamber 40 may be washed with a solution (e.g., tissue culture medium or physiological solution) to remove any remaining unbound cells, while the target cells remain bound, via magnetic attraction, as part of the complex with the magnetic separation reagent. In one embodiment wherein it is desired to culture the positively selected cells, the appropriate amount and type of tissue culture medium relative to that cell type is then introduced into the culture chamber; the magnetic sheet is then removed (e.g., by a pulling or peeling action, as illustrated in FIG. 8) from the cell culture apparatus, thereby removing the magnetic force holding the complexes in place in the culture chamber, and thereby releasing the complexes into the medium; and then the cell culture apparatus is placed into and incubated in a cell culture incubator.

EXAMPLE 4

The cell culture apparatus according to the present invention may also be used for applications in which recombinant DNA molecules are introduced into cultured cells. In this example, illustrated is the use of the cell culture apparatus in which a vector is introduced into the cells by introducing an effective amount of the vector (for introduction into the cultured cells) into the cell culture apparatus so that the vector contacts the cultured cells contained in the culture chamber of the cell culture apparatus. The methods used for introducing a substance into the cell culture apparatus, as described in Example 2 herein, may also be used to introduce the vector into the cell culture apparatus. As will be apparent to one skilled in the art, the vector may comprise a plasmid vector, viral vector, expression vector, or a combination thereof. As apparent to one skilled in the art, the vector may comprise a recombinant DNA molecule comprising the vector operatively linked (e.g., to a promoter) to a desired DNA molecule to be expressed by cells containing the vector. As known to those skilled in the art of molecular biology, animal cells (and more preferably, mammalian cells) or plant cells are typical cells into which it is desired to introduce a recombinant DNA molecule such as an expression vector for promoting expression of a desired gene into a gene product in the cells.

For example, cultured cells contained in the cell culture apparatus may be incubated with a mixture comprising an amount of a recombinant DNA molecule desired to be introduced into the cells, and a transfection reagent. The DNA molecule is mixed with the transfection reagent and the mixture comprising tissue culture medium, transfection reagent and vector is introduced through the aperture and expelled into the culture chamber so as to contact the adherent, cultured cells. The cell culture apparatus may then be incubated overnight at 37° C. in 5% $CO_2$ so that the contact between the cultured cells and the mixture (comprising the tissue culture medium and transfection reagent and vector) promote the uptake by and introduction into cultured cells of the vector. The tissue culture medium may then be removed from the cell culture apparatus, and replaced with fresh tissue culture medium. Transfection efficiency may then be determined using a conventional method known in the art, and as enabled by the vector used. As will be apparent to one skilled in the art, the transfection efficiency may be increased depending on factors which include, but are not limited to, the type of cells into which it is desired to introduce the vector, optimization of the conditions for transfection (e.g., the amount of DNA per number of cells, the medium used for transfection, the time of the transfection process), and the type and amount of transfection reagent used. Also, it will be apparent to one skilled in the art that using similar steps, a vector may also be introduced into anchorage-independent cells cultured in the cell culture apparatus according to the present invention.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept; and thus, such modifications and/or adaptations are intended to be within the meaning and scope of the appended claims.

What is claimed is:

1. A cell culture apparatus comprising:
a frame comprising a housing, and at least one aperture which comprises an opening through the frame, wherein each aperture of the at least one aperture contains a septum; at least one gas permeable membrane, wherein the at least one gas permeable membrane is securely sealed in a leak-proof sealing to the frame in forming a portion of a wall of a culture chamber; a rigid surface which forms a wall of the culture chamber, wherein the culture chamber is formed between the at least one gas permeable membrane and the rigid surface and the frame, and wherein the at least one gas permeable membrane is optically transparent and clear.

2. The cell culture apparatus according to claim 1, wherein the frame comprises 2 or more apertures.

3. The cell culture apparatus according to claim 1, wherein the portion is an amount in a range of from about 10% to about 100%.

4. The cell culture apparatus according to claim 1, wherein the portion is an amount in a range of from about 10% to about 60%.

5. The cell culture apparatus according to claim 1, wherein the at least one gas permeable membrane comprises a surface treated to improve cell attachment.

6. The cell culture apparatus according to claim 1, wherein cells are selected from the group consisting of individual cells, cells forming a tissue, and a combination thereof.

7. The cell culture apparatus according to claim 1, wherein the septum further comprises an antimicrobial agent.

8. The cell culture apparatus according to claim 7, wherein the antimicrobial agent is incorporated into elastomeric material of the septum and forms a surface coating on the septum, and wherein the antimicrobial agent exhibits migration through the elastomeric material as the surface coating of antimicrobial agent is depleted.

9. The cell culture apparatus according to claim 8, wherein the at least one gas permeable membrane and the opposing rigid surface are spaced apart by a distance in the range of from about 0.1 to about 0.5 inches.

10. The cell culture apparatus according to claim 1, wherein the frame comprises a beveled portion which slopes in relation to the plane of the at least one gas permeable membrane.

11. The cell culture apparatus according to claim 1, wherein the cell culture apparatus further comprises a magnetic sheet assembly detachably secured thereto, wherein the magnetic sheet assembly is extended over and detachably secured to cell culture apparatus in a face to face manner by placing the magnetic sheet assembly in adhesive contact with at least one gas permeable membrane which forms the culture chamber of the cell culture apparatus.

12. A bioreactor comprising a plurality of cell culture apparatuses according to claim 1, wherein a fluid passageway is provided between the plurality of cell culture apparatuses, and wherein the fluid passageway allows for fluid flow communication between culture chambers of cell culture apparatuses connected by the fluid passageway.

13. A method of culturing cells in the cell culture apparatus according to claim 1, the method comprising:
(a) suspending the cells to be cultured in an appropriate amount of tissue culture medium to support cell growth, in forming a suspension;
(b) introducing the suspension into an instrument for injecting the suspension into the cell culture apparatus;
(c) inserting a tip of the instrument through the septum and aperture, and into the cell culture chamber of the cell culture apparatus;
(d) expelling the suspension from the instrument and into the cell culture chamber;
(e) withdrawing the tip from the cell culture apparatus; and
(f) incubating the cell culture apparatus containing the suspension of medium and cells.

14. The method according to claim 13, wherein the cells to be cultured are anchorage-dependent cells.

15. The method according to claim 13, wherein the cells to be cultured are anchorage-independent cells.

16. The method according to claim 14, wherein after the anchorage-dependent cells have attached to the at least one gas permeable membrane of the cell culture apparatus in step (f), the method comprises a further step of rotating the cell culture apparatus 180° in culturing the cells in an inverted manner in the culture chamber.

17. The method according to claim 16, wherein after the anchorage-dependent cells have attached to a membrane of the cell culture apparatus in step (f), the method comprises the further steps:
(g) rotating the cell culture apparatus 180°; and
(h) repeating steps (c) through (f);
wherein both the at least one gas permeable membrane and the rigid surface serve as attachment surfaces onto which cells are cultured.

18. A method of magnetic separation using the cell culture apparatus according to claim 11, the method comprising:
(a) mixing a fluid containing a mixed population of cells in which there is a population of a cell type desired to be isolated by magnetic separation together with a magnetic separation reagent having binding specificity for the cell type desired to be separated, in forming a mixture comprising complexes between the magnetic separation reagent and cells of the type for which it has binding specificity;
(b) introducing the mixture into the culture chamber of the cell culture apparatus so that the mixture contacts a wall of the culture chamber formed by the at least one gas permeable membrane, along the plane of which is detachably secured the magnetic sheet; and
(c) incubating the mixture in the cell culture apparatus for a sufficient time for the complexes to contact and be held in position along the wall of the culture chamber due to attraction of the complexes to a magnetic field strength of the magnetic sheet.

19. The method according to claim 18, further comprising removing from the cell culture apparatus the mixture which remains unbound in the culture chamber, and wherein the removed mixture comprises cells separated by a process of negative selection.

20. The method according to claim 19, wherein after removal of the mixture, the cells comprising the complexes bound in the culture chamber and which remain in the cell culture apparatus comprise cells separated by a process of positive selection.

21. The method according to claim 20, further comprising introducing tissue culture medium into the culture chamber, removing the magnetic sheet from the cell culture apparatus, and incubating the cell culture apparatus in culturing the cells separated by the process of positive selection.

22. A method of introducing a recombinant DNA molecule into cells cultured in the cell culture apparatus according to claim 1, the method comprising:
  (a) mixing a transfection reagent with the recombinant DNA molecule comprising a vector in forming a mixture comprising the recombinant DNA molecule;
  (b) mixing the mixture comprising the recombinant DNA molecule with tissue culture medium in forming medium comprising the recombinant DNA molecule;
  (c) introducing the medium comprising the recombinant DNA molecule into the culture chamber so as to contact the cultured cells in the cell culture apparatus; and
  (d) incubating the medium comprising the recombinant DNA molecule in contact with the cultured cells in promoting introduction of the recombinant DNA molecule into cultured cells in the culture chamber.

* * * * *